United States Patent [19]

Hill

[11] Patent Number: 4,474,760

[45] Date of Patent: Oct. 2, 1984

[54] STABILIZED 2-MERCAPTOPYRIDENE-1-OXIDE AND DERIVATIVES

[75] Inventor: Nicholas J. Hill, Andover, Mass.

[73] Assignee: Excalibur, Inc., Portland, Me.

[21] Appl. No.: 506,764

[22] Filed: Jun. 22, 1983

[51] Int. Cl.$^3$ .................. A01N 25/22; A01N 43/40; A01N 55/02; A01N 55/04

[52] U.S. Cl. .................... 424/174; 424/245; 424/263

[58] Field of Search ............. 424/175, 245, 263, 174

[56] References Cited

U.S. PATENT DOCUMENTS

| | | | |
|---|---|---|---|
| 2,686,786 | 8/1954 | Shaw et al. | 424/330 |
| 2,809,971 | 10/1957 | Bernstein et al. | 424/245 |
| 3,027,372 | 3/1962 | Starrs | 424/245 |
| 3,533,993 | 10/1970 | Hovey et al. | 424/78 |
| 3,940,482 | 2/1976 | Grand | 424/245 |
| 4,161,526 | 7/1979 | Gorman | 424/145 |
| 4,171,355 | 10/1979 | Stubbs et al. | 424/331 |
| 4,363,663 | 12/1982 | Hill | 424/337 |

*Primary Examiner*—Albert T. Meyers
*Assistant Examiner*—Joyce L. Morrison
*Attorney, Agent, or Firm*—Thomas N. Tarrant

[57] ABSTRACT

A biocidal composition suitable for use as a stabilizer in polymer systems using 2-mercaptopyridene-1-oxide or a derivative combined with an organophosphorous compound and a benzotriazole wherein the organophosphorous compound and the benzotriazole act together to stabilize the mercaptopyridene against degradation and discoloration of the polymer system.

6 Claims, No Drawings

STABILIZED 2-MERCAPTOPYRIDENE-1-OXIDE AND DERIVATIVES

BACKGROUND OF THE INVENTION

1. Field of the Invention

The invention relates to antimicrobial compounds and in particular to antimicrobial compounds for use in polymeric compositions.

2. Prior Art Statement

The applicant considers the following U.S. Patents to be the most pertinent prior art known to him.

| | |
|---|---|
| 2,686,786 | Shaw & Bernstein |
| 2,809,971 | Bernstein & Losee |
| 3,027,372 | Starrs |
| 3,533,993 | Hovey |
| 4,363,663 | Hill |

The Shaw and Bernstein patent discloses both the preparation of 2-mercaptopyridine-1-oxide and its antibacterial activity.

Bernstein and Losee describe the preparation of a number of heavy metal salt derivatives of 2-mercaptopyridine-1-oxide.

Starrs discloses a tin salt derivative of 2-mercaptopyridine-1-oxide and its method of preparation. He also discloses its use as a fungicide on a number of materials.

Hovey discloses the use of 2-mercaptopyridine-1-oxide as a stabilizer of vinyl chloride resins against heat degradation.

Hill (previous patent of present inventor) discloses the use of organophosphorus compounds in preparation of antimicrobial solutions. The patent discloses that solutions containing the organophosphorus compounds produce less degradation in appearance of plastic resins in which they are utilized than the same antimicrobial agent without the organophosphorus compound.

Since 1970, when the Hovey patent was issued, fusion times have been shortened and process temperatures increased. These modern conditions of time and temperature preclude the use of 2-mercaptopyridine-1-oxide and its derivatives as thermal stabilizers or as antimicrobial compounds in plastics because they discolor any polymer system containing them. Even small amounts of ultraviolet light increase the discoloration caused by 2-mercaptopyridine-1-oxide or its derivatives in a polymer system. Heat and light stabilizers are commonly used in polymer systems, but no addition of these or ultraviolet absorbers effectively stabilizers 2-mercaptopyridine-1-oxide or a derivative against the effects of process heat or ultraviolet light.

SUMMARY OF THE INVENTION

In accordance with the invention, a mercaptopyridine-oxide biocide is provided that is stabilized against the effects of heat and ultraviolet light which a synergistic combination of an organophosphorus compound and a benzotriazole, thus permitting the use of 2-mercaptopyridine-1-oxide or a derivative as a antimicrobial protectant in a polymer system without sensitivity to discoloration.

DESCRIPTION OF THE PREFERRED EMBODIMENTS

The new compositions of the invention comprise, in each instance, a combination of a 2-mercaptopyridine-1-oxide compound (or derivative), an organophosphorous compound and a benzotriazole. The 2-mercaptopyridine-1-oxide compounds found suitable in the inventive compositions are:
2-mercaptopyridine-1-oxide; sodium-2-mercaptopyridine-1-oxide; calcium-2-mercaptopyridine-1-oxide; zinc-2-mercaptopyridine-1-oxide; antimony-2-mercaptopyridine-1-oxide; cadmium-2-mercaptopyridine-1-oxide; tin-2-mercaptopyridine-1-oxide; stannous chloride bis(-2-pyridyl-1-oxide)disulphide; di(lower alkyl)-tin-2-mercaptopyridine-1-oxide; tri(lower alkyl)tin-2-mercaptopyridine-1-oxide; triphenyltin-2-mercaptopyridine-1-oxide; and mixtures of these.

The organophosphorous compounds found suitable in the inventive compositions are:
alkyl phosphites; aryl phosphites; alkyl-aryl phosphites; mono, di, tri and polyphosphites as well as glycol phosphonates. The alkyl phosphites include: dioctyl phosphite; triisodecyl phosphite; triisooctyl phosphite; trilauryl phosphite; distearyl phosphite; tristearyl phosphite; ditridecyl phosphite; diisooctyl phosphite; and tris(dipropylene glycol)phosphite. Aryl phosphites include: diphenyl phosphite; tris nonylphenyl phosphite; and triphenyl phosphite. Alkyl-aryl phosphites include: diphenyl isodecyl phosphite; diphenyl issooctyl phosphite; phenyl diisodecyl phosphite; phenyl neopentylene glycol phosphite; ethyl hexyl diphenyl phosphite; and diisooctyl octylphenyl phosphite. Monophosphites include the monophosphites listed above. Diphosphites include: bis(neopentyl glycol)triethylene glycol diphosphite; tetrakis(nonylphenyl)polypropylene glycol diphosphite; and diphenyl didecyl(2,2',4-trimethyl-1,3-pentanediol)diphosphite. Tri and polyphosphites include: heptakis(dipropylene glycol)triphosphite and poly(dipropylene glycol)phenyl phosphite. Glycol phosphonates include bis(dipropylene glycol)dipropylene glycol phosphonate and di(amyl)amyl phosphonate.

The benzotriazole compounds found suitable for use in the inventive compositions include:
2(3',5'-bis[1-methyl-1-phenyl ethyl]-2'-hydroxyphenyl)-benzotriazole;
2(2'-hydroxy-5'-methyl phenyl)benzotriazole;
2,3(3',5'-di-t-butyl-2'hydroxyphenyl)-5-chlorobenzotriazole;
2(2'-hydroxy-3',5'-di-t-butylphenyl)benzotriazole;
2(3'-t-butyl-2'-hydroxy-5'-methyl phenyl)-5-chlorobenzotriazole;
2(2'-hydroxy-3',5'-di-t-amylphenyl)benzotriazole; and
2(2'-hydroxy-5-t-octylphenyl)benzotriazole.

Since a primary usefulness of the present compositions is as a biocidic stabilizer in polymer systems, the composition ratios and experimental examples are based on polymer system application. It will be recognized that the inventive composition is useful in other applications.

As a biocide, 2-mercaptopyridine-1-oxide or a derivative is used in a polymer system at from 0.05 weight percent to about 0.35 weight percent. Preferably the polymer system should contain from 0.1 weight percent to about 0.2 weight percent.

In order to protect 2-mercaptopyridine-1-oxide or a derivative of it in a polymer system, a combination of a phosphite or phosphonate and a benzotriazole must be present with said 2-mercaptopyridine-1-oxide or derivative. For convenience, 2-mercaptopyridine-1-oxide or its derivative (one of its metallic salts) will be frequently referred to hereafter as "the biocide" while the organo phosphite or phosphonate will be frequently referred to as the "first stabilizer" and the benzotriazole as the "second stabilizer". If the desired weight percent of the biocide is represented as "1", then the ratio of biocide to first stabilizer to second stabilizer can range from 1:0.25:1.5 to 1:1.5:0.25. The preferred ratio of biocide to first stabilizer to second stabilizer is substantially 1:1:1.

2-mercaptopyridine-1-oxide, or its metallic salts, stabilized in accordance with the invention can be used to protect coatings, adhesives, films sheets, foams and other forms of polymer systems based upon such materials as, polyvinyl chloride, vinyl chloride-vinyl acetate copolymer, ethylene vinyl acetate, polyethylene, polypropylene, acrylonitrile-butadiene-styrene (ABS) and polyurethane.

Experimental results of the invention are given in the following samples. The samples all use the same PVC plastisol since changing the particular polymer system has insignificant affect. The plastisol used was prepared by mixing the following:

|  | PARTS BY WEIGHT |
| --- | --- |
| Borden resin VC-440 | 100 |
| dioctylphthalate (plasticizer) | 50 |
| Drapex 44 (Witco plasticizer) | 5 |
| Mark 755 (Witco heat stabilizer) | 2.5 |
| stearic acid (lubricant) | 0.5 |

All the following samples used this plastisol plus additives as indicated in the description of each sample.

Sample 1

Control—no additives

Sample 2 plastisol plus 0.2 weight percent zinc-2-mercaptopyridine-1-oxide

Sample 3 plastisol, 0.2 weight percent zinc-2-mercaptopyridine-1-oxide, 0.2 weight percent poly(dipropylene glycol)phenyl phosphite, 0.2 weight percent 2(2'-hydroxy-5'-methyl phenyl)benzotriazole

Sample 4 plastisol, 0.2 weight percent zinc-2-mercaptopyridine-1-oxide, 0.2 weight percent triisodecyl phosphite, 0.2 weight percent 2(2'-hydroxy-3'-5'-di-t-butylphenyl)benzotriazole

Sample 5 plastisol, 0.2 weight percent zinc-2-mercaptopyridine-1-oxide, 0.2 weight percent tris(dipropylene glycol)phosphite, 0.2 weight percent 2(3'-t-butyl-2'-hydroxy-5'-methyl phenyl)-5-chlorobenzotriazole

Sample 6 plastisol, 0.2 weight percent zinc-2-mercaptopyridine-1-oxide, 0.2 weight percent trisnonyl phenyl phosphite, 0.2 weight percent 2,3(3',5'-di-t-butyl-2'-hydroxyphenyl)-5-chlorobenzotriazole

Sample 7 plastisol, 0.2 weight percent zinc-2-mercaptopyridine-1-oxide, 0.2 weight percent triphenyl phosphite, 0.2 weight percent 2(2'-hydroxy-3',5'-di-t-amylphenyl)benzotriazole

Sample 8 plastisol, 0.2 weight percent zinc-2-mercaptopyridine-1-oxide, 0.2 weight percent phenyl diisodecyl phosphite, 0.2 weight percent 2(3',5'-bis[1-methyl-1-phenylethyl]-2'-hydroxyphenyl)benzotriazole

Sample 9 plastisol, 0.2 weight percent zinc-2-mercaptopyridine-1-oxide, 0.2 weight percent tetraphenyl dipropyleneglycol diphosphite, 0.2 weight percent 2(2'-hydroxy-5-t-octylphenyl)benzotriazole

Sample 10 plastisol, 0.2 weight percent zinc-2-mercaptopyridine-1-oxide, 0.2 weight percent phenyl neopentylene glycolphosphite, 0.2 weight percent 2(3'-t-butyl-2'-hydroxy-5'-methylphenyl)-5-chlorobenzotriazole

Sample 11 plastisol, 0.2 weight percent zinc-2-mercaptopyridine-1-oxide, 0.05 weight percent poly(dipropylene glycol)phenyl phosphite, 0.3 weight percent 2(2'-hydroxy-5'-methyl phenyl)benzotriazole

Sample 12 plastisol, 0.2 weight percent zinc-2-mercaptopyridine-1-oxide, 0.05 weight percent phenyl neopentylene glycol phosphite 0.3 weight percent 2(3'-t-butyl-2'-hydroxy-5'-methyl phenyl)-5-chlorobenzotriazole.

Sample 13 plastisol, 0.2 weight percent zinc-2-mercaptopyridine-1-oxide, 0.3 weight percent poly(dipropylene glycol)phenyl phosphite, 0.05 weight percent 2(2'-hydroxy-5'-methylphenyl)benzotriazole

Sample 14 plastisol, 0.2 weight percent zinc-2-mercaptopyridine-1-oxide, 0.3 weight percent phenyl neopentylene glycol phosphite, 0.05 weight percent 2(3'-t-butyl-2'-hydroxy-5'-methyl phenyl)-5-chlorobenzotriazole

Sample 15 plastisol, 0.1 weight percent zinc-2-mercaptopyridine-1-oxide, 0.2 weight percent 2(2'-hydroxy-5'-methyl phenyl)benzotriazole

Sample 16 plastisol, 0.2 weight percent zinc-2-mercaptopyridine-1-oxide, 0.2 weight percent poly(dipropylene glycol)phenyl phosphite.

All samples were fused at 425° F. for ten minutes. The sample sheets were divided into four parts. One part was oven aged for sixty minutes at 350° F. A second part was exposed to UV light for 100 hours. A third part was exposed to UV light for 200 hours. The fourth section was not subjected to heat or UV light.

Limited test results are given here for biocidal activity since the biocidal activity of the present biocide is well documented and is as would be expected.

The samples were compared for color change before and after being stressed by heat and/or UV light. The results are shown in TABLE I.

TABLE I

| Sample Number | As is | 60 Min. @ 350° F. | 100 Hrs. UV | 200 Hrs. UV |
|---|---|---|---|---|
| 1 | NC* | yellow tinge | NC | yellow tinge |
| 2 | NC | orange | lt. brown | brown |
| 3 | NC | NC | NC | NC |
| 4 | NC | NC | NC | NC |
| 5 | NC | NC | NC | NC |
| 6 | NC | NC | NC | NC |
| 7 | NC | NC | NC | NC |
| 8 | NC | NC | NC | NC |
| 9 | NC | NC | NC | NC |
| 10 | NC | NC | NC | NC |
| 11 | NC | yellow tinge | NC | yellow tinge |
| 12 | NC | yellow tinge | NC | yellow tinge |
| 13 | NC | NC | yellow tinge | yellow tinge |
| 14 | NC | NC | yellow tinge | yellow tinge |
| 15 | NC | yellow | yellow | yellow |
| 16 | NC | yellow | yellow | yellow |

*NC means no color

Samples 3 through 13 pass standard microbiology laboratory petri dish tests against Aspergillus niger. Sample 1 fails. Samples 2, 15 and 16 pass on as "as is" basis but fail after heat and/or UV light stressing.

Additional evaluations were made using standard plastics stabilizers such as metallic soaps, thioesters, phenolics, amines, benzophenones and combinations thereof. All such stabilizers and combinations of them failed to stabilize the mercaptopyridine oxide biocide against degradation by heat and light.

While the present invention has been described with respect to specific embodiments, variations within the skill of the art are contemplated. For example, combinations or mixtures of the different biocide derivatives are useable as are combinations or mixtures of the listed organophosphorous compounds and combinations or mixtures of the listed benzotriazoles. Thus it is the intention to cover the invention as set forth in the following claims.

I claim:
1. An antimicrobial composition comprising:
(a) a biocide selected from the group consisting of 2-mercaptopyridine-1-oxide, sodium-2-mercaptopyridine-1-oxide, calcium-2-mercaptopyridine-1-oxide, zinc-2-mercaptopyridine-1-oxide, antimony-2-mercaptopyridine-1-oxide, cadmium-2-mercaptopyridine-1-oxide, tin-2-mercaptopyridine-1-oxide, stannous chloride bis(-2-pyridyl-1-oxide)disulphide, di(lower alkyl)tin-2-mercaptopyridine-1-oxide, tri(lower alkyl)tin-2-mercaptopyridine-1-oxide, triphenyltin-2-mercaptopyridine-1-oxide and mixtures of these;
(b) a first stabilizer comprising an organic phosphorous compound selected from the group consisting of alkyl phosphites, aryl phosphites, alkyl-aryl phosphites, di, tri and poly phosphites and glycol phosphonates and a combination thereof; and,
(c) a second stabilizer comprising a benzotriazole compound selected from the group consisting of 2(3',5'-bis[1-methyl-1-phenyl ethyl]-2'-hydroxyphenyl)benzotriazole; 2(2'-hydroxy-5'-methyl phenyl)benzotriazole; 2,3(3',5'-di-t-butyl-2'-hydroxyphenyl)-5-chlorobenzotriazole; 2(2'-hydroxy-3',5'-di-t-butylphenyl)benzotriazole; 2(3'-t-butyl-2'-hydroxy-5'-methyl phenyl)-5-chlorobenzotriazole; 2(2'-hydroxy-3',5'-di-t-amylphenyl)benzotriazole; and, 2(2'-hydroxy-5-t-octylphenyl)benzotriazole, wherein with the weight percent of the biocide taken as "1", the ratio of biocide to first stabilizer to second stabilizer is in the range of 1:0.25:1.5 to 1:1.5:0.25.

2. An antimicrobial composition according to claim 1 wherein said first stabilizer and said second stabilizer together are substantially twice the weight of said biocide.

3. An antimicrobial composition according to claim 2 wherein each of said first stabilizer and said second stabilizer has at least 25% the weight of said biocide.

4. An antimicrobial composition according to claim 1 wherein each of said first stabilizer and said second stabilizer has at least 25% the weight of said biocide.

5. An antimicrobial composition according to claim 1 wherein said biocide is zinc-2-mercaptopyridine-1-oxide.

6. An antimicrobial stabilizing composition for polymer systems comprising zinc-2-mercaptopyridine-1-oxide as a biocide and a combination of two stabilizers for the biocide consisting of poly(dipropylene glycol)phenyl phosphite and 2(2'-hydroxy-5'-methyl phenyl)benzotriazole wherein with the weight percent of the biocide taken as "1", the range of proportions is 1:0.25:1.5 to 1:1.5:0.25 and wherein said two stabilizers act synergistically to prevent degradation and discoloration of the polymer system due to the biocide.

* * * * *